United States Patent [19]

Harms et al.

[11] Patent Number: 5,297,234
[45] Date of Patent: Mar. 22, 1994

[54] METHOD AND APPARATUS FOR THE RAPID THERMAL PROCESSING OF TRANSFUSION FLUID

[75] Inventors: Frank H. Harms, Marietta, Ga.; John R. Beard, Memphis, Tenn.; Alexander Duncan, Dunwoody, Ga.

[73] Assignee: LifeSource Advanced Blood Bank Systems, Inc., Atlanta, Ga.

[21] Appl. No.: 521,185

[22] Filed: May 9, 1990

[51] Int. Cl.$^5$ .............................................. A61F 7/00
[52] U.S. Cl. ..................................... 392/470; 604/114; 392/379
[58] Field of Search ............... 219/400, 302, 296, 299, 219/303; 604/113, 114; 165/102, 30; 422/46; 392/470, 360–361, 375–376, 354–356, 379; 62/407, 372

[56] References Cited

U.S. PATENT DOCUMENTS

| 3,338,233 | 8/1967 | Grosholz et al. | 219/400 |
| 3,480,015 | 11/1969 | Gonzales | 219/302 |
| 3,564,202 | 2/1969 | Oppenheim | 219/400 |
| 3,586,097 | 6/1971 | Bender et al. | 165/30 |
| 3,634,651 | 1/1972 | Siegel et al. | 392/470 |
| 4,019,260 | 4/1977 | Levy et al. | 34/3 |
| 4,034,740 | 7/1977 | Atherton et al. | 236/1 |
| 4,117,881 | 10/1978 | Williams et al. | 219/302 |
| 4,154,861 | 5/1979 | Smith | 219/400 |
| 4,309,592 | 1/1982 | Le Boeuf | 219/302 |
| 4,336,435 | 6/1982 | Kashyap et al. | 219/10.55 F |
| 4,339,928 | 7/1982 | Guibert | 62/62 |
| 4,459,825 | 7/1984 | Cronch | 62/407 |
| 4,470,264 | 9/1984 | Morris | 62/372 |
| 4,473,739 | 9/1984 | Scheiwe et al. | 366/209 |
| 4,485,641 | 12/1984 | Angelier et al. | 62/407 |
| 4,522,586 | 6/1985 | Price | 432/11 |
| 4,642,441 | 2/1987 | Kenyon | 219/501 |
| 4,707,587 | 11/1987 | Greenblatt | 219/302 |
| 4,731,072 | 3/1988 | Aid | 604/408 |
| 4,742,202 | 5/1988 | Campbell et al. | 219/10.55 F |
| 4,855,555 | 8/1989 | Adams et al. | 604/114 |
| 4,874,915 | 10/1989 | Harms et al. | 219/10.55 F |
| 4,892,030 | 1/1990 | Grieve | 219/400 |
| 5,081,697 | 1/1992 | Manella | 392/496 |
| 5,123,477 | 6/1992 | Tyler | 165/2 |
| 5,225,161 | 7/1993 | Mathewson | 165/183 |

FOREIGN PATENT DOCUMENTS

| 706487 | 3/1965 | Canada | 219/411 |
| 62-189073 | 8/1987 | Japan . | |
| 2014583 | 8/1979 | United Kingdom . | |
| 91/01638 | 2/1991 | World Int. Prop. O. . | |

Primary Examiner—Bruce A. Reynolds
Assistant Examiner—John A. Jeffery
Attorney, Agent, or Firm—Warren L. Franz

[57] ABSTRACT

The temperature of bags of blood or blood components is varied by directing a heated or refrigerated flow of air through vents (138) of pairs of opposing ducts (130A, 130B) longitudinally spaced across gaps to present thermal processing chambers (136) into which the bags are received. The vents are centrally located on vertical tubes (132) laterally separated by vertical air return slots (135), and act to direct the airflow substantially perpendicular and with turbulence against the bags. In a described thermal processing unit (110), the spacings of the vents and tubes are chosen to match the corresponding spacing of vertical tubular chambers (62) of a preferred bag (10) with which the unit (110) can be used. A central system automatically regulates airflow temperature in accordance with bag internal core temperature measurements taken externally of the bags by a sensor (140) having a sensing tip (142) that is pressed inwardly into bag flexible sheet material (11, 12) when airflow is present, and retracted when airflow is stopped.

32 Claims, 3 Drawing Sheets

METHOD AND APPARATUS FOR THE RAPID THERMAL PROCESSING OF TRANSFUSION FLUID

TECHNICAL FIELD

The present application relates generally to the thermal processing of a packaged liquid, and relates more specifically to a method and an apparatus for the rapid and hygienic freezing and subsequent rapid and hygienic thawing of fresh-frozen blood and blood component transfusion fluids.

BACKGROUND OF THE INVENTION

A readily available supply of plasma and whole blood is an essential requirement of any medical trauma treatment facility. Since plasma can be stored at room temperature for a matter of only a few hours before spoilage occurs, it is conventional practice to freeze blood components. Whole blood can be stored only forty days before spoilage occurs and hence must be frozen if storage for longer periods is anticipated. Typically, plasma and whole blood are frozen within six hours after collection, in polyvinyl chloride bags holding about 300 milliliters. The fresh-frozen plasma is subsequently stored at temperatures of around −30° C., and fresh-frozen whole blood is stored at temperatures of around −80° C. When properly frozen, blood and blood components may be stored for up to ten years.

While the procedure of fresh-freezing blood and blood components has essentially solved the problems of storage, the process of thawing the product for use presents certain difficulties. When whole blood or platelets are being thawed, possible damage to cells during thawing is a major concern. While post-thaw viability of cellular structures is not of concern in thawing plasma, the viability of coagulation proteins is of primary importance. The most widely accepted method of thawing fresh-frozen blood and blood components comprises immersing the bag in a warm water bath. By completely surrounding the bag in a 30° C.-37° C. water bath and agitating it periodically, a single bag or "unit" of frozen plasma may be thawed usually in thirty to forty-five minutes.

This procedure presents a number of problems. First, immersing the bag in a non-sterile water bath may contaminate the bag ports, such that the thawed blood or blood components are tainted as they are withdrawn from the bag. Immersing the bag in a warm water bath can also cause any labels affixed to the bag to become detached. Even if the labels remain attached to the bag, the warm water bath often causes the labels to become wrinkled, such that it becomes impossible to scan a bar code which may be imprinted on the label. Additionally, any interruption in the integrity of the bag can permit an exchange of water and plasma, thereby contaminating both the product and the water bath. The most common form of interruption in the integrity of the bag is "edge damage" resulting from impact of the bag edges with any hard object while at low temperatures. This results in fracture of the PVC bags in 5–10% of all bags produced. Further, the water bath process cannot be accelerated, such as by exposing the blood or blood components to a higher temperature bath, since subjecting frozen plasma to any larger thermal gradient in an effort to speed up the procedure can result in physical stress and possible damage to the normal protein configuration of the plasma, and since subjecting whole blood or platelets to a higher thermal gradient can possibly damage cellular structures. The requirement of a thawing period of from thirty to forty-five minutes renders the use of frozen blood or blood components impractical for emergency trauma cases, where the patient may have an immediate need for the product and cannot afford the luxury of waiting for frozen blood or blood components to be thawed. Medical facilities cannot anticipate possible needs of blood and blood components by thawing a number of units in advance, since the requirement that each unit be typed and cross-matched to the specific patient for which it is intended would require thawing an inordinate number of units which would not be used. Furthermore, since the product cannot be safely refrozen once thawed, units which are thawed in anticipation of possible use must be discarded if the anticipated use does not arise.

Accordingly, there is a need to provide a hygienic method and apparatus for the thawing of fresh-frozen blood and blood components which does not expose the ports or the contents of the bag to the possibility of contamination.

There is also a need to provide a method and apparatus for the thawing of fresh-frozen blood and blood components which is sufficiently rapid that the product can be kept frozen until only moments before it is actually needed.

A number of efforts have been made to adapt microwave ovens for thawing frozen blood components which are contained in a bag. Some of these efforts have involved attempts to adapt a conventional cavity-type microwave oven, of the type widely used for cooking foods, for use in thawing such blood components. However, conventional prior art microwave blood-thawing devices tend to thaw the blood unevenly, which can result in overheating localized portions of the blood while other portions of the blood remain frozen.

The apparatus disclosed in my prior U.S. Pat. No. 4,874,915 overcomes many of the shortcomings associated with previous devices for thawing blood and blood components with microwave illumination. The bag of frozen blood or blood components is placed within a membrane surrounded by a liquid dielectric material which is impedance-matched with the frozen product. The membrane and liquid dielectric material readily conform to the surface of the blood bag to eliminate impedance mismatches at the various interfaces. In the disclosed embodiment, a substantially uniform magnetic field is created by employing a waveguide which supports only odd-numbered harmonic wavelengths and by utilizing an RF lens to disperse the waves across the width of the blood bag. Thus, nonuniform heating resulting from standing waves caused by reflections or from uneven illumination is substantially eliminated, thereby providing uniform heating of the frozen product.

However, the apparatus and method disclosed in my aforementioned U.S. Pat. No. 4,874,915 suffers certain disadvantages common to microwave thawing devices, namely high cost, mechanical complexity, and limited portability. In certain instances, small medical facilities which may have a need for a readily available supply of blood or blood components may not be able to afford the considerable cost of a microwave blood warming device. Further, the mechanical complexity necessitates maintenance costs and may possibly cause the unit to break down at an inopportune time. Finally, microwave thawing devices do not lend themselves to ready portability.

Thus, there is a need to provide a method and apparatus for the rapid thawing of blood and blood components which can be made available to medical facilities at a relatively low cost.

There is also a need to provide a method and apparatus for the rapid thawing of blood and blood components which is mechanically simple so as to eliminate maintenance costs and substantially reduce the possibility of malfunction at an inopportune time.

There is yet another need to provide a method and apparatus for the rapid thawing of blood and blood components which is highly portable.

Conventional blood freezing apparatus presents further problems with the length of time required to freeze whole blood and plasma contained therein. Factor 8, the primary clotting factor in blood, deteriorates rapidly at room temperature. Absent expensive high-speed liquid immersion freezing equipment, freezing whole blood or plasma in a conventional blood freezing apparatus does not occur rapidly enough to prevent deterioration of a significant proportion of the Factor 8.

Thus, there is a need to provide a method and apparatus for freezing whole blood and plasma which is sufficiently rapid that deterioration of Factor 8 is reduced.

SUMMARY OF THE INVENTION

As will be seen, the present invention satisfies each of these needs unfulfilled by prior art freezing and thawing apparatus for blood and blood components. Stated generally, the present invention comprises a method and apparatus for the rapid and hygienic thawing of frozen blood or blood components which does not expose the ports or the contents of the bag to the possibility of contamination. The disclosed apparatus is sufficiently rapid that the frozen blood or blood components can be kept frozen until only moments before they are actually needed. The apparatus is mechanically simple, thereby eliminating maintenance costs and reducing the probabilities of equipment failure at inopportune moments. The apparatus does not require an extensive capital investment and can thus be made readily available to even the smallest of medical facilities. Finally, the apparatus is highly portable.

Stated somewhat more specifically, the present invention comprises an apparatus for thawing a bag of frozen blood or blood components. The apparatus includes a means for holding the bag of frozen blood or blood components. The apparatus further includes a means for creating a flow of air and a means for heating the flow of air. The flow of heated air is directed to impinge upon the surface of the bag so as to thaw the contents thereof. The apparatus further includes a means for measuring the temperature of the frozen blood or blood components. In the disclosed embodiment, the flow of heated air is directed at the bag in such a manner as to cause a turbulent airflow at the air/bag interface, thereby to increase the heat transfer between the bag and the air. Also in the disclosed embodiment, a control system automatically monitors the detected temperature and terminates the thawing procedure when the temperature reaches 30° C.

In another aspect, the present invention comprises an apparatus for the rapid freezing of blood and blood components. A bag of blood or blood components is introduced into the apparatus. The apparatus includes a means for creating a flow of air and a means for refrigerating the airflow. The flow of chilled air is then directed to impinge upon the surface of the bag to freeze the blood or blood components therein. Temperature measuring means measures the temperature of the blood or blood components. In the disclosed embodiment, the flow of chilled air is directed at the bag in such a manner as to cause a turbulent airflow at the air/bag interface, thereby to increase the heat transfer between the bag and the air. Also in the disclosed embodiment, a control system automatically monitors the detected temperature and terminates the freezing procedure when the temperature of the bag contents reaches $-30°$ C.

Thus, it is an object of the present invention to provide an improved apparatus for the thermal processing of blood and blood components.

It is another object of the present invention to provide a hygienic method and apparatus for the thawing of fresh-frozen blood and blood components which does not expose the ports or the contents of the bag to the possibility of contamination.

Yet another object of the present invention is to provide a method and apparatus for the thawing of fresh-frozen blood and blood components which is sufficiently rapid that the product can be kept frozen until only moments before it is actually needed.

Still another object of the present invention is to provide a method and apparatus for freezing whole blood and plasma which is sufficiently rapid that deterioration of Factor 8 is reduced.

It is a further object of the present invention to provide a method and apparatus for the rapid thawing of blood and blood components which can be made available to medical facilities at a relatively low cost.

Another object of the present invention is to provide a method and apparatus for the rapid thawing of blood and blood components which is mechanically simple so as to eliminate maintenance costs and substantially reduce the possibility of malfunction at an inopportune time.

Still another object of the present invention is to provide a method and apparatus for the rapid thawing of blood and blood components which is highly portable.

Other objects, features, and advantages of the present invention will become apparent upon reading the following specification, when taken in conjunction with the drawings and the appended claims.

BRIEF DESCRIPTION OF THE DRAWINGS

FIG. 5 is a schematic diagram of the control system of the apparatus of FIG. 3.

DETAILED DESCRIPTION OF THE DISCLOSED EMBODIMENT

Figure 1:
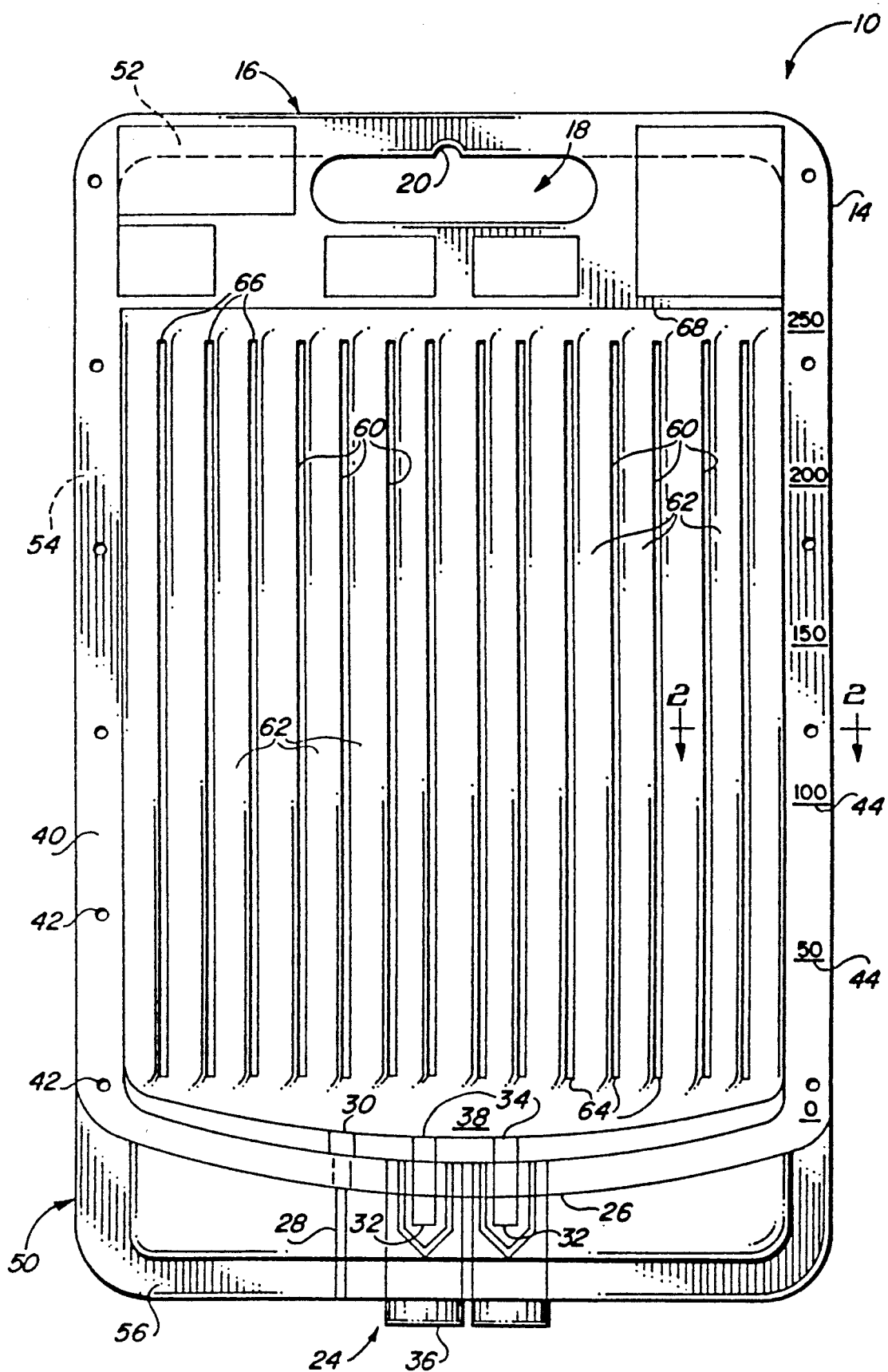
FIG. 1 is a front view of a blood bag for use with the apparatus of the present invention.
Figure 2:
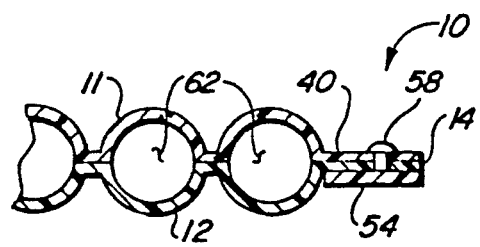
FIG. 2 is an enlarged partial transverse section view of the blood bag of FIG. 1 taken along lines 2—2 of FIG. 1.

Referring now to the drawings, in which like numerals indicate like elements throughout the several views, FIGS. 1 and 2 illustrate an improved blood bag 10 according to the present invention. The bag 10 is comprised of front and back sheets or panels 11, 12 of 0.012 inch thick polyvinyl chloride film. The front and back sheets are ultrasonically welded, heat sealed, glued, or otherwise bonded around their marginal edges 14 to form a flexible, watertight container. The mutually facing surfaces of the front and back sheets 11, 12 are textured to eliminate interlayer cohesion which might interfere with the uniform filling of the bag. The exterior surfaces of the bag may also be textured to facilitate handling. The bag 10 further includes a top "billboard" section 16 which includes space for the standard Red Cross label set. The top section 16 includes a handle portion 18 and central hanger notch 20 for hanging the bag.

A conventional blood bag transfusion and filling port set, shown generally at 24, is located at the bottom 26 of the bag 10. The port set 24 is identical to that used on the Model 4R1423 plasma bag marketed by Fenwall Corporation. The port set 24 includes a transfer tube 28 which communicates with the interior of the bag 10 through a loading port 30. In addition, a pair of sterile transfusion tubes 32 communicate with the interior of the bag via corresponding transfusion ports 34. The transfusion tubes 32 are sealed within a seal 36 formed by opposing polymeric sheets in the manner well known to those skilled in the art to maintain the sterility of the tubes until use. The interior of the bag 10 has a generally concave bottom 38 with the ports 30, 34 disposed at the base of the concavity such that when the bag is hung in an upright position the contents of the bag are funnelled toward the ports.

Along the sides of the bag are attachment areas 40 which in the disclosed embodiment are approximately ⅝ inches wide. The front and back sheets 11, 12 are preferably sealed together across the entire width of the attachment areas 40, and a plurality of holes 42 are formed within the attachment areas at spaced-apart intervals down each side of the bag 10. A vertical scale 44 is imprinted on at least one of the bag attachment areas 40 to indicate the volume of fluid in the bag 10.

A rigid frame 50 includes a top portion 52 which spans the top of the bag 10, depending side members 54 which extend down each side of the bag, and a bottom member 56 joining the lower ends of the side members 54. The side members 54 each include a plurality of pins 58 having enlarged head portions slightly larger than the holes 42 along the sides of the bag 10 and at spaced-apart intervals to correspond to the location of the holes 42. The rigid frame 50 is removably mounted to the bag 10 by fitting each of the holes 42 along the sides of the bag onto a corresponding pin 58 on the side members 54 of the frame. When the frame 50 is mounted to the bag, the lower end of the frame extends below the bottom of the bag to protect the lower end of the bag and the transfusion and filling port set 24 from possible damage.

The front and back sheets 11, 12 of the bag 10 are ultrasonically welded or heat sealed together along a number of vertical seal lines 60 at spaced apart intervals across the width of the bag. In the disclosed embodiment, the seal lines 60 are approximately 0.625 inches on center when the bag is in its flattened, unfilled state. As can be seen in FIG. 2, when fluid is introduced into the bag, the areas between adjacent seal lines 60 are filled and expand into tubular chambers 62 which are approximately 0.375 inches in diameter. The seal lines 60 terminate at their lower ends 64 at locations spaced upwardly from the bottom 38 of the bag 10 and at their upper ends 66 at locations spaced downward from the top 68 of the bag. The spaced apart relation between the ends 64, 66 of the seal lines 60 and the respective top 68 and bottom 38 of the bag 10 places each of the tubular chambers 62 in communication with the other chambers 62 at both its upper and lower ends. This intercommunication permits the bag 10 to fill and to drain uniformly, whether the bag is in its upright or inverted orientation.

The collection of blood and blood components into the bag 10 will now be explained. The bag 10 with the rigid frame 50 mounted thereto is hung by its hanger notch 20 on a hook or the like. The bag is filled with whole blood or blood products via the transfer tube 28 and corresponding loading port 30. The textured mutually facing surfaces of the front and back sheets 11, 12 eliminate interlayer cohesion and prevents the sheets from sticking together, thus promoting the easy and uniform filling of the bag. As the bag fills, the chambers 62 defined within the bag by the seal lines 60 expand to a generally tubular shape, as depicted in FIG. 2. The distance by which the front and back sheets 11, 12 can separate under the outward pressure exerted by the fluid is constrained by the seal lines 60, such that the maximum thickness of the bag is controlled as the bag fills. Since the lower and upper ends 64, 66 of the seal lines 60 are spaced apart from the corresponding lower and upper ends 38, 68 of the bag 10, the bag fills uniformly across its width as fluid is introduced into the interior of the bag.

Figure 3:
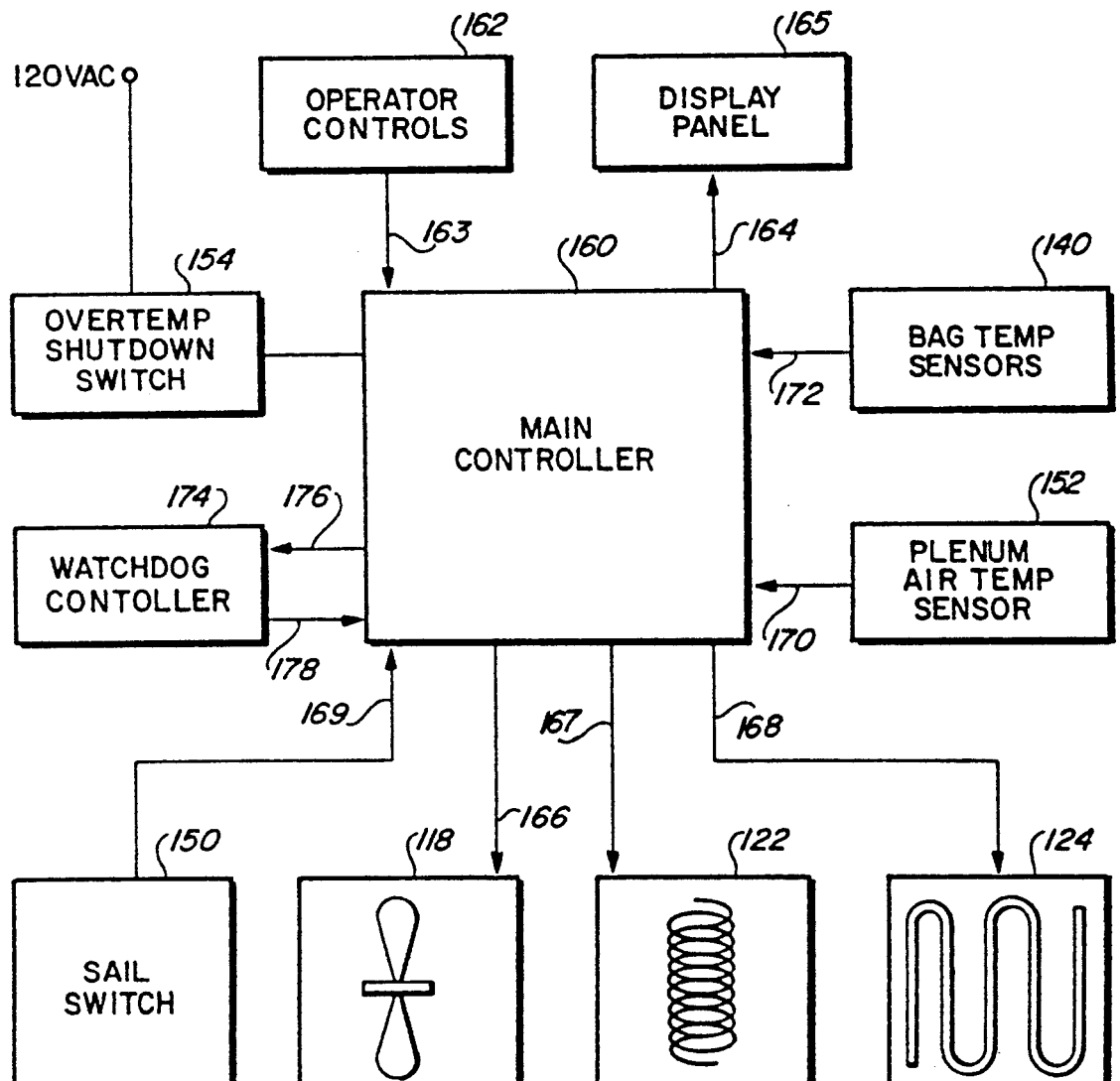
FIG. 3 is a side elevation view of an apparatus according to the present invention for the freezing and thawing of the blood bag of FIG. 1.
Figure 3:
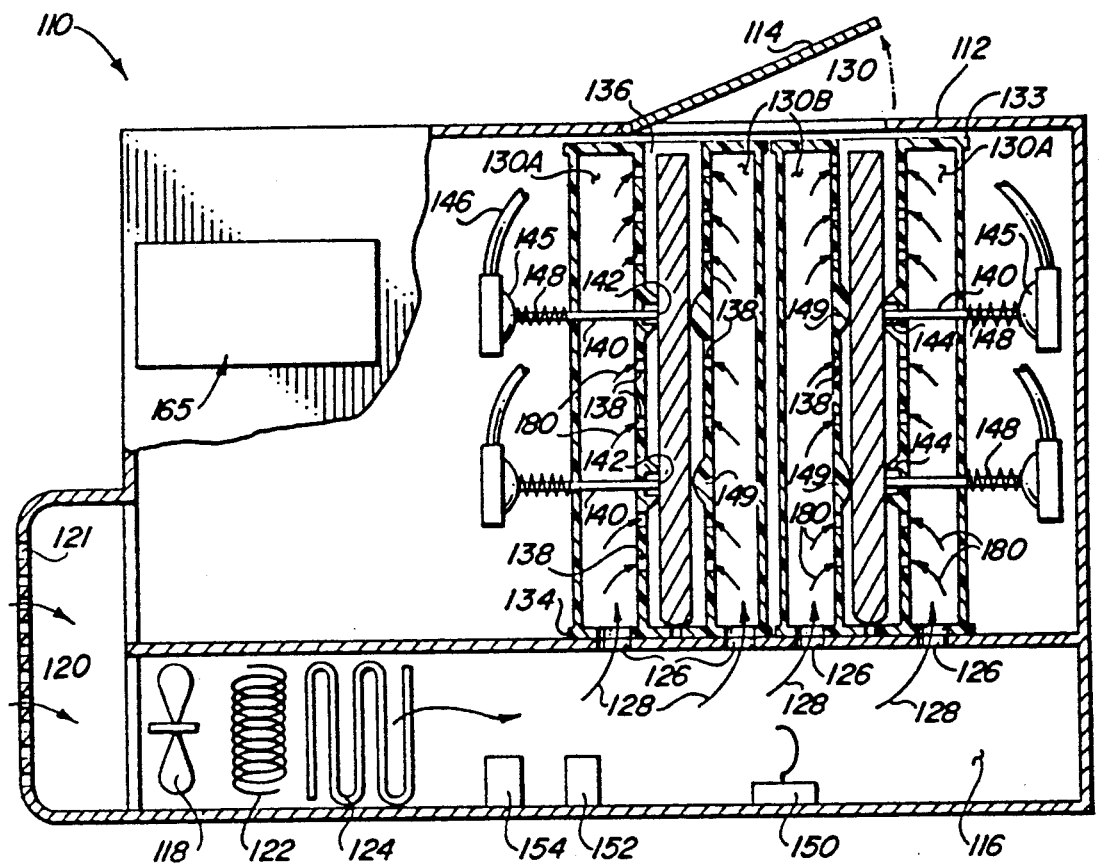
Figure 4:
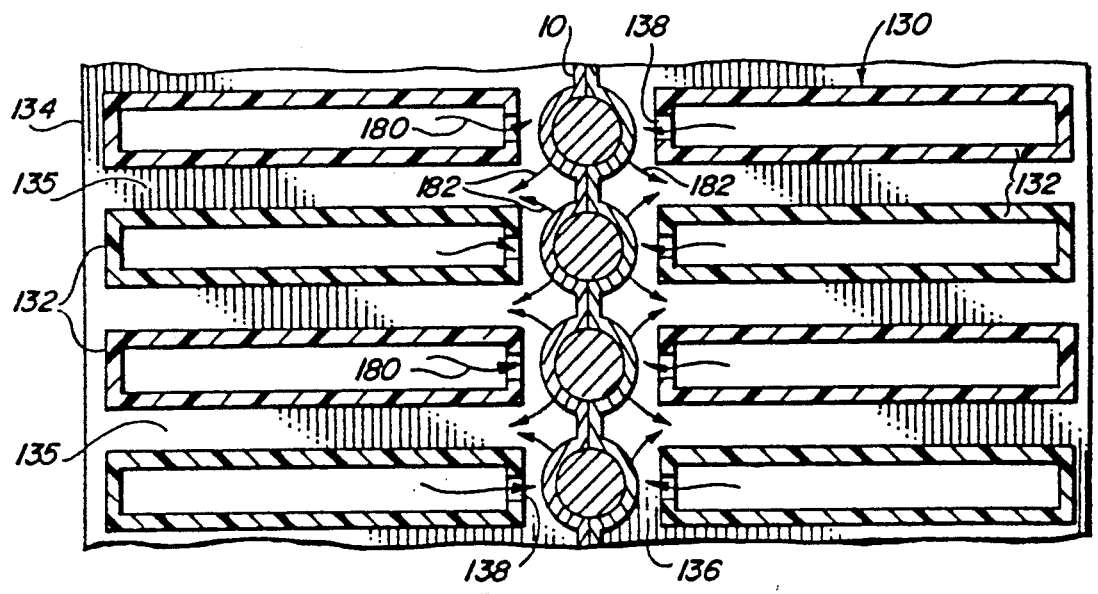
FIG. 4 is a partial top view of the duct component of the apparatus of FIG. 3.

Referring now to FIGS. 3-5, a blood bag freezing and thawing unit 110 includes a housing 112 having a hinged lid 114 on its upper surface. In the base of the housing 112 is a plenum 116. A fan 118 driven by a conventional electric motor (not shown) is located at the left end of the plenum 116 and draws a flow of air (indicated by the arrows 120) from the housing through a vent 121 in the housing 112 and into the plenum 116. The air is blown past a conventional electrical resistive-type heating coil 122 and a conventional refrigeration-evaporator cooling coil 124 toward the right side of the plenum 116. The air flow is then directed upwardly and out through four slots 126 in the upper wall of the plenum 116, as indicated by the arrows 128.

Resting on top of the plenum 116 are two pairs of generally vertical ducts 130, each of which pairs comprises an outer duct 130A and an inner duct 130B. As can be seen in FIG. 4, each duct 130 comprises fifteen vertical tubes 132 comprised of thin-walled Plexiglass or the like. The tubes 132 are maintained in parallel, spaced-apart relation by means of upper and lower brackets 133, 134, also of Plexiglass or other suitable material. In the disclosed embodiment, each tube is generally rectangular in cross section and measures 0.25 inches wide by 2.0 inches deep, and the tubes are 0.375 inches on center. Thus, each adjacent pair of tubes defines a vertical slot 135 therebetween which is approximately 0.125 inches wide. The height and width of the ducts 130 substantially corresponds to the height and width of a bag 10, and each pair of ducts 130 is spaced apart by a distance sufficient to receive a vertically oriented blood bag 10 therebetween, thus defining a vertical thermal processing chamber 136 between the outer and inner ducts 130A, 130B.

The ducts 130 rest on top of the plenum 116 and are aligned with the slots 126 in the upper wall of the plenum so that the air exiting through the slots 126 is directed upwardly through the tubes 132. The lower bracket 134 blocks the lower end of the vertical slots 135 between adjacent tubes 132, thereby ensuring that the air exiting through the slots 126 will flow upwardly through the tubes rather than between them.

Each pair of ducts 130 has a plurality of vents 138 located on mutually facing portions thereof so as to direct a flow of air against the adjacent surface of the blood bag 10 disposed within the vertical chamber 136 between the ducts 130A, 130B. The vents 138 of the disclosed embodiment are circular holes 0.0625 inches in diameter. This dimension is selected to achieve a relationship between the size of the vents 138 and the cross-sectional area of the vertical tubes 132 which will provide a substantially equal exit airflow through each of the vents 138 irrespective the the location of the vent along its tube.

Each outer duct 130A includes upper and lower bag temperature sensors 140. The sensing tip 142 of the sensors 140 faces inwardly and is surrounded by an insulative spacer 143 which protects and thermally isolates the sensor. Above and below each insulative spacer 143 are deflectors 144 which are bevelled to deflect the edge of a blood bag 10 being inserted into or withdrawn from the apparatus 110, again to protect the sensors 140 from damage. Each sensor 140 projects through its corresponding duct 130A and extends outwardly thereof. A diaphragm 145 is operatively associated with each sensor 140 and is in communication with the interior of the ducts 130A by means of an air line 146. A coil spring 148 is disposed around each sensor 140 and biases the sensor outwardly. Air flowing through the ducts 130A inflates the diaphragm 145 and moves the corresponding sensor 140 inwardly, overcoming the force of the associated coil spring 148 and biasing the sensor tip 142 into intimate contact with the mutually facing surface of the bag 10. A stop element 149 on the mutually facing surface of the corresponding inner duct 130B prevents the bag 10 from being displaced away from the temperature sensor 140. When the airflow through the ducts 130A is discontinued, the diaphragm 145 is no longer actuated, and the coil springs 148 bias the sensors 140 outwardly, retracting the sensor tip 142 and its insulative spacer 143.

Located within the plenum 116 is a sail switch 150 for detecting airflow within the plenum. Also located within the plenum 116 is a plenum temperature sensor 152. Finally, a bimetal overtemp shutdown switch 154 is located within the plenum and is operatively associated with the electrical system of the apparatus 110 in the manner to be hereinbelow described.

FIG. 5 schematically depicts the control system 158 of the apparatus 110. A microprocessor-based main controller 160 receives signals from operator controls 162. These controls 162 include a start switch for starting the procedure, a two-position push/pull switch for determining whether a thawing or freezing procedure is to be performed, and an emergency stop switch. The main controller also sends signals via signal path 164 to an operator display panel 165, which includes a temperature display and an alarm for audibly alerting the operator.

The main controller 160 also controls the operation of the fan 118, the heating coil 122, and the cooling coil 124 via signal paths 166, 167, and 168 respectively. The sail switch 150 located within the plenum 116 monitors the airflow within the plenum and sends a signal to the main controller 160 via signal path 169. The main controller constantly monitors the sail switch 150 and powers the heating coil 122 or cooling coil 124 only when proper airflow is detected. The plenum temperature sensor 152 is disposed within the plenum 116 and sends a signal to the main controller 160 via a signal path 170. During a thawing procedure, the main controller 160 monitors the plenum temperature detected by the plenum temperature sensor 152 and powers the heating coil on or off as necessary to maintain the air temperature in the plenum at 35° C. Finally, the bimetallic overtemp shutdown switch 154 is wired into the electric circuit powering the thawing unit 110 and monitors the plenum temperature, interrupting the electrical power to the apparatus if the plenum temperature exceeds 40° C.

During a thawing or freezing procedure, the controller 160 continuously receives signals from each of the bag temperature sensors 140 via a signal path 172. The controller 160 constantly monitors the bag temperatures and sends a signal to the operator display panel 165 via the signal path 164 to display the bag temperatures. The main controller 160 also constantly monitors the operator controls 162 and shuts down the apparatus 110 if activation of the emergency stop button is detected. When the temperature of the bags reaches 30° C. in a thawing cycle or −30° C. in a freezing cycle, the controller shuts down the heating coil 122 or cooling coil 124 and signals the operator via the operator display 165 that the procedure is complete. At the termination of a thawing cycle, the controller 160 is programmed to continue running the fan 118 for five seconds after the heating coil 122 is deactivated to dissipate heat remaining in the coil. Similarly, at the termination of a freezing cycle, the fan 118 will continue to run for five seconds to evaporate the refrigerant remaining in the evaporator coil 124.

During both the heating and the cooling procedures, a watchdog controller 174 constantly monitors the activities of the main controller 160 via signal path 176. If the watchdog monitor 172 detects any abnormality, the watchdog monitor sends a signal via signal path 178 to shut down the apparatus 110.

Operation of the apparatus to freeze a bag 10 of frozen blood or blood products will now be described. The operator opens the door 114 in the top of the housing 112 and lowers a bag 10 of frozen blood or blood products into the thawing chamber 136 between one of the pairs of ducts 130. If only a single bag 10 is to be frozen, the bag may be placed into the chamber 136 defined by either of the pairs of ducts 130. If two bags 10 are to be frozen simultaneously, one bag is lowered into each chamber 136. The bevelled deflectors 144 above each bag temperature sensor 140 bias the lower edge of the bag 10 inwardly and protect the sensor tip 142 from damage. With the bags 10 thus positioned within the apparatus 110, the operator actuates the controls 162 to initiate the freezing process.

Upon receiving the signal from the operator controls 162 to initiate the freezing procedure, the main controller 160 actuates the fan 118. When the sail switch 150 detects the necessary minimum airflow within the plenum 116, the controller 160 actuates the refrigeration coil 122. The fan 118 draws air from the housing 112 and into the plenum 116 in the direction indicated by the arrows 120. The air is blown past the refrigeration coil 122, cooling the air.

The flow of refrigerated air is then forced through the slots 126 in the upper wall of the plenum 116 and into the ducts 130 to flow upwardly through the tubes 132, as indicated by the arrows 128. As the tubes 132 fill with air, the diaphragms 145 are pressurized and bias the bag temperature sensors 140 inwardly until the sensor tip 142 is brought into intimate contact with the adjacent surface of the bag 10. The stop elements 149 on the mutually facing surface of the opposite duct 130B hold the bag 10 in place and prevent the bag from being displaced away from the bag temperature sensors 140.

Meanwhile, the refrigerated air flows out the vents in the ducts 130 to impinge upon the adjacent surface of the bag 10, as indicated by the arrows 180. In the disclosed embodiment, the impinging air is travelling at a velocity of sixty to seventy miles per hour. The stream of air then flows through the vertical slots 135 between adjacent tubes 132, as indicated by the arrows 182, and away from the bag 10.

The contents of the bag 10 are rapidly cooled by the flow of refrigerated air impinging upon the surface of the bag. In the disclosed embodiment, the contents of the bag 10 are uniformly chilled to a temperature of −30° C. in approximately five minutes. When the highest temperature detected by any of the bag temperature sensors 140 is −30° C., the main controller 160 shuts off the power to the refrigeration coil 124 and signals the operator audibly and visually that the cycle is complete. The fan 118 continues to run for approximately five seconds after the cooling coil 124 is deactivated to dissipate residual refrigerant in the evaporator coil 124. When the fan 118 shuts off, the diaphragms 145 are no longer pressurized, and the coil springs 148 retract the sensors 140 and their respective insulative spacers 143 away from the surface of the bag 10. The operator then opens the lid 114 in the top of the housing 112 and withdraws the bags of frozen blood from the apparatus 110. The deflectors 144 deflect the bag 10 toward the center of the chamber 136 as the bag is withdrawn from the unit, thereby protecting the sensor tip 142. The frozen blood is now transported to conventional refrigerated storage facilities.

Operation of the same apparatus to thaw a bag 10 of frozen blood or blood products will now be described. The operator opens the door 114 in the top of the housing 112 and lowers a bag 10 of frozen blood or blood products into the chamber 136 between one of the pairs of ducts 130 in the same manner hereinabove described with respect to the freezing process. With the bags 10 thus positioned within the apparatus 110, the operator actuates the controls 162 to initiate the thawing process.

Upon receiving the signal from the operator controls 162 to initiate a thawing procedure, the main controller 160 actuates the fan 118. When the sail switch 150 detects the necessary minimum airflow within the plenum 116, the controller 160 actuates the heating coil 122. The fan 118 draws air from the housing 112 and into the plenum 116 in the direction indicated by the arrows 120. The air is blown past the heating coil 122, heating the air. The plenum temperature sensor 152 senses the air temperature within the plenum 116 and signals the main controller 160. If the plenum air temperature is below 35° C., the main controller 160 cycles the heating element 122 on. If the plenum air temperature is above 35° C., the main controller 160 cycles the heating element 122 off. Thus, the main controller 160 is operative to regulate the heating element 122 to maintain an air temperature of approximately 35° C.

The flow of heated air is then forced through the slots 126 in the upper wall of the plenum 116 and into the ducts 130 to flow upwardly through the tubes 132, as indicated by the arrows 128. As the tubes 132 fill with air, the diaphragms 145 are pressurized and bias the bag temperature sensors 140 inwardly until the sensor tip 142 is brought into intimate contact with the adjacent surface of the bag 10. The stop elements 149 on the mutually facing surface of the opposite duct 130B hold the bag 10 in place and prevent the bag from being displaced away from the bag temperature sensors 140.

Meanwhile, the heated air flows out the vents in the ducts 130 to impinge upon the adjacent surface of the bag 10, as indicated by the arrows 180. In the disclosed embodiment, the impinging air is travelling at a velocity of sixty to seventy miles per hour. The stream of air then flows through the vertical slots 135 between adjacent tubes 132, as indicated by the arrows 182, and away from the bag 10. The constant flow of air impinging upon the surface of the bag 10 and then being carried away prevents the air at the bag interface from ever reaching the dew point, thus preventing condensation on the surface of the bag.

The frozen contents of the bag 10 are rapidly heated by the flow of heated air impinging upon the surface of the bag. As the contents of the bag 10 begin to thaw, the constant pressure exerted by the energized diaphragms 145 biases the tip 142 of the sensors 140 inwardly so as to provide a temperature reading near the core of the bag 10. In the disclosed embodiment, the contents of the bag 10 are uniformly warmed to a temperature of 30° C. in approximately four minutes. When the bag temperature sensors 140 detect a temperature of 30° C., the main controller 160 shuts off the power to the heating coil 122 and signals the operator audibly and visually that the cycle is complete. The fan 118 continues to run for approximately five seconds after the heating coil 122 is deactivated to dissipate residual heat in the heating coil and plenum 116. When the fan 118 shuts off, the diaphragms 145 are no longer pressurized, and the coil springs 148 retract the sensors 140 and their respective insulative spacers 143 and away from the surface of the bag 10. The operator then opens the lid 114 in the top of the housing 112 and withdraws the bags of frozen blood from the apparatus 110. The deflectors 144 deflect the bag 10 toward the center of the chamber 136 as the bag is withdrawn from the unit, thereby protecting the sensor tip 142. When the bag is removed from the unit 110, it is ready for immediate use. The seals 36 at the bottom of the bag are pulled apart to expose the transfusion ports 34, and the bag is thereafter used in a conventional manner.

It will be appreciated that the control system of the apparatus 110 provides a number of safety features. First, the controller 160 cuts power to the heating and cooling coils 122, 124 if the sail switch 150 fails to detect the proper airflow within the plenum 116. Thus, if the fan 118 fails, or if the air flow through the system is obstructed, the heating and cooling elements 122, 124 are deactivated, thereby preventing a possibly dangerous overheating situation. Second, during a thawing cycle, the main controller 160 constantly monitors the plenum air temperature sensor 152 and powers down the heating coil 122 when the plenum temperature exceeds 35° C., a second safeguard against possible overheating of the apparatus 110. Finally, if both the sail switch 150 and the plenum air temperature sensor 152 fail, the bimetallic switch 154 will interrupt electrical power to the thawing unit 110 if the temperature within the plenum 116 ever reaches 40° C.

One feature of the apparatus 110 of the present invention which contributes to enhanced freezing and thawing rates is that the chilled or heated airflow is directed at the surface of the bag so as to create turbulence at the surface of the bag. In contrast to laminar airflow found, for example, in conventional blast freezers, this turbulent airflow increases the rate of heat exchange between the air and the bag, thus markedly lowering freezing and thawing times.

Another feature of the apparatus 110 of the present invention is that during the thawing procedure, the airflow impinging upon the bag flows at such a high rate of speed that the temperature of the air at the bag interface never falls below the dew point. This feature provides the advantage that it prevents the buildup of a layer of condensation on the surface of the bag, which layer of condensation could serve as an insulating barrier and inhibit the thawing procedure.

The improved freezing capacity of the apparatus 110 not only reduces the time required to freeze whole blood and plasma but also increases the amount of Factor 8, the primary clotting factor in blood, present in the frozen product. The improved freezing time reduces the amount of time the contents of the bag are exposed to moderate temperatures and thus reduces the deterioration of Factor 8. The resulting quick-frozen blood or plasma thus includes an increased amount of Factor 8 over blood or plasma frozen in conventional refrigeration equipment.

While the invention has been hereinabove described with respect to a particular embodiment of an apparatus 110, it will be understood that many modifications are possible without departing from the scope of the present invention. For example, rather than the vents in the ducts comprising a plurality of circular holes, narrow slots can be formed in the duct walls to direct the flow of air against the surface of the bag. The bag may be vibrated or otherwise agitated during thawing to increase the rate of heat exchange, or the nozzles may be oscillated or the airflow pulsed to enhance the rate of thaw. Infrared temperature sensors may be used in place of the thermocouple sensors of the disclosed embodiment. Solenoids may be used in place of the air-actuated diaphragms to move the temperature sensors into contact with the bag. Or, relay logic may be employed to control the thawing or freezing process, rather than the microprocessor-based control system of the disclosed embodiment.

While the present invention has been disclosed with respect to a unit 110 which both thaws and freezes, it will be appreciated that a unit capable only of thawing can be provided simply by eliminating the refrigeration coil, or that a unit intended only for freezing can be provided by eliminating the heating coil. Further, while the apparatus 110 is especially designed for use with a thin bag 10 of the type hereinabove described, it will be appreciated that the apparatus will also provide improved results with conventional blood bags in comparison to conventional air thawing procedures. It is anticipated that a conventional blood bag could be thawed in the apparatus 110 in approximately twenty minutes.

Finally, it will be understood that the preferred embodiment has been disclosed by way of example, and that other modifications may occur to those skilled in the art without departing from the scope and spirit of the appended claims.

What is claimed is:

1. Apparatus for the thermal processing of a container of transfusion fluid; said container comprising first and second sheets of flexible material joined at intervals to present a plurality of laterally spaced tubular chambers having internal cores and being filled with the transfusion fluid; said apparatus comprising:
   a housing defining a cavity;
   means, located on said housing, for creating a flow of air;
   means, located on said housing, for controlling temperature of the flow of air;
   means, located on said housing, for directing the temperature controlled flow of air into said cavity; said directing means comprising first and second pluralities of tubes communicated to receive the temperature controlled flow of air and located in said cavity, spaced longitudinally across a gap; the tubes of each of said first and second pluralities having vents and being laterally separated by slots having positions corresponding to said intervals of said container; and
   means for removably mounting said container within said gap, with said first sheet adjacent said first plurality of tubes, said second sheet adjacent said second plurality of tubes, and said chambers respectively aligned with said tubes;
   said tubes, vents and slots being relatively dimensioned, configured and positioned so that the temperature controlled air will be directed through said vents to impinge on said sheets substantially perpendicular to said chambers and to exit through said slots.

2. Apparatus as in claim 1, further comprising means, located on said housing, for measuring temperature of the fluid at said cores; said temperature measuring means comprising a plurality of temperature sensor tips, and means for respectively urging said tips externally onto said container at said chambers when said container is mounted within said gap.

3. Apparatus as in claim 2, further comprising means, responsive to temperature measured by said temperature measuring means, for regulating said airflow temperature controlling means.

4. Apparatus as in claim 2, wherein said temperature measuring means further comprises means for retracting said tips out of contact with said container for enabling unobstructed removal of said container from said gap.

5. Apparatus as in claim 4, further comprising means for detecting absence of the flow of air; and wherein said means for retracting said tips is responsive to detection of said absence by said airflow absence detecting means.

6. Apparatus as in claim 1, wherein said means for mounting said container comprises a rigid frame, means for securing said container peripherally to said rigid frame; and means for mounting said frame within said gap.

7. Apparatus as in claim 1, wherein said sheets are joined at uniform intervals to present said chambers; said vents of said tubes have centers laterally spaced by amounts equal to said uniform intervals; and said tubes are laterally separated by slots of lateral dimension equal to one-third of said uniform intervals.

8. Apparatus as in claim 7, wherein said vents are identical openings dimensioned and configured to provide an airflow exit velocity of sixty to seventy miles per hour.

9. Apparatus as in claim 1, wherein said chambers have heights and widths, and said tubes have heights and widths coextensive with said heights and widths of said chambers.

10. Apparatus as in claim 9, wherein said tubes are rectangular in cross-section.

11. Apparatus as in claim 1, wherein said airflow creating means comprises a fan, and an electric motor for driving said fan.

12. Apparatus as in claim 11, wherein said housing further has a plenum, said fan is connected to draw air from outside said housing into said plenum, and said airflow temperature controlling means comprises a heat transfer member located in said plenum.

13. Apparatus as in claim 12, wherein said housing has a base, said plenum is located in said base, said plenum has an upper wall with first and second slots, said first plurality of tubes is communicated with said first slot, and said second plurality of tubes is communicated with said second slot.

14. Apparatus as in claim 13, wherein said tubes are oriented vertically in said cavity, and said container mounting means comprises rigid frame means for mounting said container with said front and back sheets oriented vertically respectively adjacent said first and second plurality of tubes.

15. Apparatus as in claim 14, wherein said tubes have a cross-sectional area, said vents are circular holes of given diameter, and said given diameter is chosen relative to said cross-sectional area to provide a substantially equal exit airflow through each of said vents irrespective of location of a particular vent on its corresponding tube.

16. Apparatus as in claim 1, further comprising a temperature sensor associated with said first plurality of tubes; said sensor comprising a sensor tip, an insulated spacer mounting said sensor tip on said housing facing toward said second plurality of tubes, and means operatively associated with said sensor for moving said sensor tip externally onto said first sheet inwardly at one of said chambers, so as to provide a temperature reading near said core of said one of said chambers.

17. Apparatus as in claim 16, wherein said means for moving said sensor tip onto said first sheet moves said sensor tip in response to creation of said air flow by said airflow creating means.

18. Apparatus as in claim 17, wherein said means for moving said sensor tip comprises a diaphragm; a coil spring biasing said sensor tip away from said first sheet; and means for inflating said diaphragm by said airflow communicated to said tubes, for moving said sensor tip against the bias of said spring in response to said diaphragm inflation.

19. Apparatus as in claim 16, further comprising deflectors mounted adjacent said spacer on said housing for deflecting said container away from said sensor when said container is inserted into or withdrawn from said gap.

20. Apparatus as in claim 19, further comprising a stop element spaced across said gap from said sensor for preventing displacement of said container away from said sensor when said sensor tip is moved into contact with said first sheet.

21. Apparatus for the thermal processing of transfusion fluid contained within a container having a flexible sheet and a central core; said apparatus comprising:
   a housing defining a cavity;
   means, located on said housing, for creating a flow of air;
   means, located on said housing, for controlling temperature of the flow of air;
   means, located on said housing, for directing the temperature controlled flow of air into said cavity; said directing means comprising first and second pluralities of tubes communicated to receive the temperature controlled flow of air and located in said cavity, spaced longitudinally across a gap; the tubes of each of said first and second pluralities having vents and being laterally separated by slots;
   said tubes, vents and slots being relatively dimensioned, configured and positioned so that the temperature controlled air will be directed through said vents to impinge on said container inserted within said gap, and to exit through said slots; and
   means, located on said housing, for measuring temperature of the fluid; said temperature measuring means comprising at least one sensor tip, and means for insulating said sensor tip and for urging said tip onto said flexible sheet of said container, when said container is within said gap, so as to provide a temperature reading near said core of said 22. Apparatus as in claim 21, further comprising means, responsive to temperature measured by said temperature measuring means, for regulating said airflow temperature controlling means.

23. Apparatus as in claim 22, wherein said temperature measuring means further comprises means for retracting said sensor tip out of contact with said container for enabling unobstructed removal of said container from said gap.

24. Apparatus as in claim 23, further comprising means for detecting absence of the flow of air, and said means for retracting said tips is responsive to detection of said absence by said airflow absence detecting means.

25. A method for the thermal processing of transfusion fluid; said method comprising:
   providing a container having first and second sheets of flexible material joined at intervals to present a plurality of laterally spaced tubular chambers having internal cores;
   providing first and second pluralities of tubes spaced longitudinally across a gap; the tubes of each of said first and second pluralities having vents and being laterally separated by slots;
   filling said chambers with transfusion fluid;
   creating a flow of air;
   controlling temperature of said flow of air;
   directing said temperature controlled flow of air through said tubes and out from said vents against said first and second sheets so that air impinges substantially perpendicular, centrally of each chamber and exits away from said sheets at said joinder intervals through said slots;
   measuring temperature of said fluid near said core of at least one of said chambers, by urging a tip of a sensor externally onto one of said sheets at said at least one of said chambers; and
   regulating said temperature controlling step, responsive to said temperature measurement.

26. A method for the thermal processing of transfusion fluid contained in a flexible container having first and second external surfaces and an internal core; said method comprising:
   providing first and second pluralities of tubes spaced longitudinally across a gap; the tubes of each of said first and second pluralities having vents and being laterally separated by slots located at intervals between said vents;
providing a temperature sensor having a sensor tip;
inserting said container within said gap, with said first surface adjacent said first plurality of tubes and said second surface adjacent said second plurality of tubes;
creating a flow of air;
directing said flow of air through said tubes and out from said vents to impinge substantially perpendicular respectively upon said adjacent first and second surfaces so as to effect heat transfer and prevent condensation at said surfaces, and so as to exit away from said sheets through said slots;
urging said sensor tip externally onto said container to take temperature measurements of said fluid near said core; and
controlling temperature of said airflow through said tubes in response to said temperature measurements.

27. A method as in claim 26 for thermal processing of transfusion fluid contained in a container further having said first and second surfaces joined at intervals to present a plurality of laterally spaced tubular chambers; wherein, in said inserting step, said container is inserted within said gap with said chambers respectively centered on said vents and said joinder intervals centered on said slots.

28. A method as in claim 27 for thawing a container further comprising a bag of frozen blood or blood components; wherein, in said flowing step, said air is flowed past a heating element to heat the air before it is flowed out of said vents; and wherein, in said controlling step, said heating element is controlled to stop heating the air when the measured bag core temperature reaches 30° C.

29. A method as in claim 28, wherein, in said controlling step, said heating element is controlled, while air is being heated, to maintain air temperature at 35° C.

30. A method as in claim 29, wherein in said temperature sensor providing step, a second temperature sensor is provided; said method further comprises taking temperature measurements of said airflow prior to flowing out from said vents; and wherein, in said controlling step, said heating element is controlled to stop heating the air when the measured airflow temperature exceeds 40° C.

31. A method as in claim 27 for freezing a container further comprising a bag of blood or blood components; wherein, in said flowing step, said air is flowed past a cooling element to cool the air before it is flowed out of said vents; and wherein, in said controlling step, said cooling element is controlled to stop cooling the air when the measured bag core temperature reaches −30° C.

32. A method as in claim 26; wherein, in said flowing step, the air is flowed out from said vents to impinge upon said surfaces at a velocity of sixty to seventy miles per hour.

* * * * *